(12) United States Patent
Mathews et al.

(10) Patent No.: US 6,803,463 B2
(45) Date of Patent: Oct. 12, 2004

(54) PROCESS FOR THE PREPARATION OF PYRAZOLOPYRIDINE DERIVATIVES

(75) Inventors: Neil Mathews, London (GB); Richard Anthony Ward, Stevenage (GB); Andrew Jonathan Whitehead, Harlow (GB)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 10/168,002

(22) PCT Filed: Dec. 20, 2000

(86) PCT No.: PCT/EP00/13001
§ 371 (c)(1),
(2), (4) Date: Jun. 14, 2002

(87) PCT Pub. No.: WO01/46194
PCT Pub. Date: Jun. 28, 2001

(65) Prior Publication Data
US 2003/0078267 A1 Apr. 24, 2003

(30) Foreign Application Priority Data
Dec. 22, 1999 (GB) .............................. 9930358

(51) Int. Cl.⁷ .................. C07D 487/04; C07D 237/08; C07C 317/22
(52) U.S. Cl. .................. 544/224; 544/236; 568/31
(58) Field of Search .................. 544/224, 236; 568/31

(56) References Cited

U.S. PATENT DOCUMENTS

| | | | |
|---|---|---|---|
| 4,985,444 A | 1/1991 | Shiokawa et al. | |
| 5,155,114 A | 10/1992 | Shiokawa et al. | |
| 5,296,490 A | 3/1994 | Shiokawa et al. | |
| 5,300,478 A | 4/1994 | Michaely et al. | |
| 5,498,774 A | 3/1996 | Mitsudera et al. | |
| 5,552,422 A | 9/1996 | Gauthier et al. | |
| 5,700,816 A | 12/1997 | Isakson et al. | |
| 5,990,148 A | 11/1999 | Isakson et al. | |
| 6,136,839 A | 10/2000 | Isakson et al. | |
| 6,451,794 B1 * | 9/2002 | Beswick et al. | 514/248 |
| 6,498,166 B1 * | 12/2002 | Campbell et al. | 514/300 |
| 2003/0008872 A1 * | 1/2003 | Beswick et al. | 514/248 |
| 2003/0040517 A1 * | 2/2003 | Beswick et al. | 514/248 |

FOREIGN PATENT DOCUMENTS

| | | |
|---|---|---|
| EP | 364204 A1 | 4/1990 |
| EP | 404190 B1 | 6/1990 |
| EP | 404190 A1 | 6/1990 |
| EP | 467248 B1 | 1/1992 |
| JP | 58 134094 | 8/1983 |
| WO | WO 9100092 | 1/1991 |
| WO | WO 9119497 | 12/1991 |
| WO | WO95 00501 A | 1/1995 |
| WO | WO96 06840 A | 3/1996 |
| WO | WO96 21667 A | 7/1996 |
| WO | WO96 31509 A | 10/1996 |
| WO | WO 9641625 | 12/1996 |
| WO | WO 9641626 | 12/1996 |
| WO | WO96 41645 A | 12/1996 |
| WO | WO 9912930 | 3/1999 |
| WO | WO 0114375 A1 | 3/2001 |

OTHER PUBLICATIONS

Zhao, Liqin; Yang, Zhi; Zhang, Shoufang, Yaoxue Xuebao, 36(4), 258–261 (Chinese) 2001.*
Talley, J.J., Selective Inhibitors of Cyclooxygenase–2 Expert opinion on Therapeutic Patents, vol. 7, No. 1, Jan. 1997, pp. 55–62.
Carter, J.S., "Recently Reported Inhibitors of Cyclooxygenase–2" Expert Opinion on Therapeutic Patents, vol. 8, No. 1, Jan. 1998, pp. 21–29.

(List continued on next page.)

Primary Examiner—Emily Bernhardt
Assistant Examiner—Thomas McKenzie
(74) Attorney, Agent, or Firm—Lorie Ann Morgan

(57) ABSTRACT

A process for the preparation of a compound of formula (I)

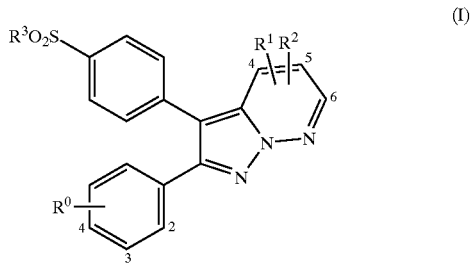

and pharmaceutically acceptable derivatives thereof in which:

$R^0$ is halogen, $C_{1-6}$alkyl, $C_{1-6}$alkoxy, $C_{1-6}$alkoxy substituted by one or more fluorine atoms, or $O(CH_2)_n NR^4R^5$;

$R^1$ and $R^2$ are independently selected from H, $C_{1-6}$alkyl, $C_{1-6}$alkyl substituted by one or more fluorine atoms, $C_{1-6}$alkoxy, $C_{1-6}$hydroxyalkyl, $SC_{1-6}$alkyl, $C(O)H$, $C(O)C_{1-6}$alkyl, $C_{1-6}$alkylsulphonyl, $C_{1-6}$alkoxy substituted by one or more fluorine atoms, $O(CH_2)_nCO_2C_{1-6}$alkyl, $O(CH_2)_nSC_{1-6}$alkyl, $(CH_2)_nNR^4R^5$, $(CH_2)_nSC_{1-6}$alkyl or $C(O)NR^4R^5$; with the proviso that when $R^0$ is at the 4-position and is halogen, at least one of $R^1$ and $R^2$ is $C_{1-6}$alkylsulphonyl, $C_{1-6}$alkoxy substituted by one or more fluorine atoms, $O(CH_2)_nCO_2C_{1-6}$alkyl, $O(CH_2)_nSC_{1-6}$alkyl, $(CH_2)_nNR^4R^5$ or $(CH_2)_nSC_{1-6}$alkyl, $C(O)NR^4R^5$;

$R^3$ is $C_{1-6}$alkyl or $NH_2$;

$R^4$ and $R^5$ are independently selected from H, or $C_{1-6}$alkyl or, together with the nitrogen atom to which they are attached, form a 4–8 membered saturated ring; and n is 1–4.

8 Claims, No Drawings

OTHER PUBLICATIONS

Talley, J.J., "5 Selective Inhibitors of Cycloxygenase–2 (COX–2)" Progress in Medicinal Chemistry, vol. 36, 1999, pp. 201–234.

Roy, P., A New Series of Selective Cox–2 Inhibitors; 5,6–Diarylthiazolo [3,2–b][1,22,4] Triazoles, Bioorganic & Med. Chem. Ltrs, vol. 7, No. 1, 1997, pp. 57–62.

Therien, M., Synthesis and Biological Evaluation of 5,6–Diarylimidazo[2.1–b] Thiazole As Selective Cox–2 Inhibitors, Bioorganic & Med. Chem. Ltrs. vol. 7, No. 1, 1997, pp. 47–52.

Akahane, A., Discovery of 6–Oxo–3–(2–Phenylprazolo[1,5–a]pyridin–3–yl)–1 (6H)–pyridazinebutanoic Acid (FR 838): A Novel Non–Xanthine Adenosine A1 Receptor Antagonist with Potent Diuretic Activity, Journal of Medicinal Chemistry, vol. 42, No. 5, 1999, pp. 779–783.

Katritzky, A.R., "Comprehensive Heterocyclic Chemistry, vol. 5," 1984, Pergamon Press, Oxford, GB, pp. 339–340.

Katritzky, A.R., "Comprehensive Heterocylcic Chemistry II, vol. 8", 1996, Pergamon Press, Oxford, GB, pp. 362.

* cited by examiner

PROCESS FOR THE PREPARATION OF PYRAZOLOPYRIDINE DERIVATIVES

CROSS-REFERENCES TO RELATED APPLICATIONS

This application is a Rule 371 Application of PCT Application No. EP00/13001, filed Dec. 20, 2000, which claims priority to GB Application Serial No. 9930358.8, filed Dec. 22, 1999.

This invention relates to a process for the preparation of pyrazolopyridazine derivatives and to intermediates for use therein.

Pyrazolopyridazine derivatives of formula (I)

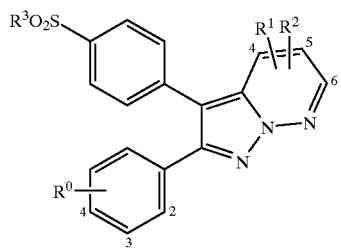

(I)

and pharmaceutically acceptable derivatives thereof in which:

$R^0$ is halogen, $C_{1-6}$-alkyl, $C_{1-6}$alkoxy, $C_{1-6}$alkoxy substituted by one or more fluorine atoms, or $O(CH_2)_n NR^4 R^5$;

$R^1$ and $R^2$ are independently selected from H, $C_{1-6}$alkyl, $C_{1-6}$alkyl substituted by one or more fluorine atoms, $C_{1-6}$alkoxy, $C_{1-6}$hydroxyalkyl, $SC_{1-6}$alkyl, $C(O)H$, $C(O)C_{1-6}$alkyl, $C_{1-6}$-alkylsulphonyl, $C_{1-6}$alkoxy substituted by one or more fluorine atoms, $O(CH_2)_n CO_2 C_{1-6}$alkyl, $O(CH_2)_n SC_{1-6}$alkyl, $(CH_2)_n NR^4 R^5$, $(CH_2)_n SC_{1-6}$alkyl or $C(O)NR^4 R^5$; with the proviso that when $R^0$ is at the 4-position and is halogen, at least one of $R^1$ and $R^2$ is $C_{1-6}$alkylsulphonyl, $C_{1-6}$-alkoxy substituted by one or more fluorine atoms, $O(CH_2)_n CO_2 C_{1-6}$alkyl, $O(CH_2)_n SC_{1-6}$alkyl, $(CH_2)_n NR^4 R^5$ or $(CH_2)_n SC_{1-6}$alkyl, $C(O)NR^4 R^5$;

$R^3$ is $C_{1-6}$alkyl or $NH_2$;

$R^4$ and $R^5$ are independently selected from H, or $C_{1-6}$alkyl or, together with the nitrogen atom to which they are attached, form a 4–8 membered saturated ring;

and n is 1–4;

are disclosed in international patent application publication no. WO99/12930, incorporated herein by reference.

By pharmaceutically acceptable derivative is meant any pharmaceutically acceptable salt, solvate or ester, or salt or solvate of such ester, of the compounds of formula (I), or any other compound which upon administration to the recipient is capable of providing (directly or indirectly) a compound of formula (I) or an active metabolite or residue thereof.

It will be appreciated that, for pharmaceutical use, the salts referred to above will be the physiologically acceptable salts, but other salts may find use, for example in the preparation of compounds of formula (I) and the physiologically acceptable salts thereof.

Suitable pharmaceutically acceptable salts of the compounds of formula (I) include acid addition salts formed with inorganic or organic acids, preferably inorganic acids, e.g. hydrochlorides, hydrobromides and sulphates.

The term halogen is used to represent fluorine, chlorine, bromine or iodine.

The term 'alkyl' as a group or part of a group means a straight or branched chain alkyl group, for example a methyl, ethyl, n-propyl, i-propyl, n-butyl, s-butyl or t-butyl group.

The compounds of formula (I) are potent and selective inhibitors of COX-2. They are of interest for use in human and veterinary medicine, particularly in the treatment of the pain (both chronic and acute), fever and inflammation of a variety of conditions and diseases.

Several processes for the preparation of the compounds of formula (I) are disclosed in WO99/12930.

The present invention provides a particularly advantageous process of preparing compounds of formula (I), not hitherto specifically disclosed, which comprises oxidation of a corresponding dihydro-pyrazolopyridazine.

Accordingly, in a first aspect, the instant invention provides a process for the preparation of a compound of formula (I) which comprises oxidising under conventional conditions a compound of formula (II)

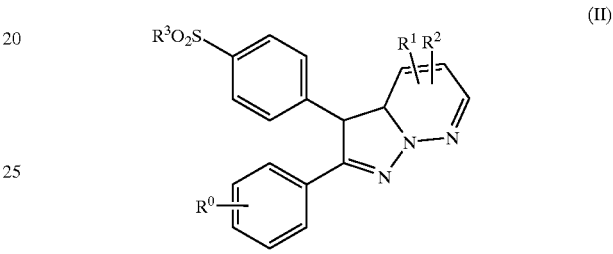

(II)

wherein $R^0$ to $R^3$ are as defined for formula (I).

Conveniently the oxidation is effected in a solvent, such as a halogenated alkane (e.g. dichloromethane); at ambient to elevated temperature, such as from 20° C. to reflux (e.g. at about 25° C.); and in the presence of a catalyst, such as activated carbon, or a transition metal catalyst (e.g. palladium on activated carbon). Alternatively, the catalyst may be replaced by an oxidising agent, such as a source of oxygen (e.g. air), or iodine.

The process according to the invention is surprisingly advantageous, being easy to carry out and proceeding in good yield.

As will be appreciated by those skilled in the art, the preparation of pharmaceutically acceptable derivatives of formula (I) may conveniently be effected by a process which comprises oxidising under conventional conditions a corresponding derivative of formula (II).

In another aspect the invention provides a process for preparing a compound of formula (I) where $R^0$ is at the 3- or 4-position of the phenyl ring, as defined in formula (I).

In another aspect the invention provides a process for preparing a compound of formula (I) where $R^1$ is at the 6-position of the pyridazine ring, as defined in formula (I).

In another aspect the invention provides a process for preparing a compound of formula (I) where $R^0$ is F, $C_{1-3}$alkyl, $C_{1-3}$alkoxy, $C_{1-3}$alkoxy substituted by one or more fluorine atoms, or $O(CH_2)_{1-3} NR^4 R^5$; or, more preferably, $R^0$ is F, $C_{1-3}$alkoxy or $C_{1-3}$alkoxy substituted by one or more fluorine atoms.

In another aspect the invention provides a process for preparing a compound of formula (I) where $R^1$ is $C_{1-4}$alkylsulphonyl, $C_{1-4}$alkoxy substituted by one or more fluorine atoms, $O(CH_2)_{1-3} CO_2 C_{1-4}$alkyl, $O(CH_2)_{1-3} SC_{1-4}$alkyl, $(CH_2)_{1-3} NR^4 R^5$, $(CH_2)_{1-3} SC_{1-4}$alkyl or $C(O)NR^4 R^5$ or, when $R^0$ is $C_{1-6}$alkyl, $C_{1-6}$alkoxy, $O(CH_2)_n NR^4 R^5$, may also be H; or, more preferably, $R^1$ is $C_{1-4}$alkylsulphonyl, $C_{1-4}$alkoxy substituted by one or more fluorine atoms or, when $R^0$ is $C_{1-6}$alkyl, $C_{1-6}$alkoxy, $C_{1-6}$alkoxy substituted by one or more fluorine atoms, or $O(CH_2)_n NR^4 R^5$, may also be H.

In another aspect the invention provides a process for preparing a compound of formula (I) where $R^2$ is H.

In another aspect the invention provides a process for preparing a compound of formula (I) where $R^3$ is methyl or $NH_2$.

In another aspect the invention provides a process for preparing a compound of formula (I) where $R^4$ and $R^5$ are independently $C_{1-3}$alkyl or, together with the nitrogen atom to which they are attached, form a 5–6 membered saturated ring.

In another aspect the invention provides a process for preparing a compound of formula (I) where n is 1–3, more preferably 1 or 2.

In another aspect the invention provides a process for preparing one group of compounds of formula (I) (group A) wherein: $R^0$ is F, $C_{1-3}$alkyl, $C_{1-3}$alkoxy, $C_{1-3}$alkoxy substituted by one or more fluorine atoms, or $O(CH_2)_nNR^4R^5$; $R^1$ is $C_{1-4}$alkylsulphonyl, $C_{1-4}$alkoxy substituted by one or more fluorine atoms, $O(CH_2)_nCO_2C_{1-4}$alkyl, $O(CH_2)_nSC_{1-4}$alkyl, $(CH_2)_nNR^4R^5$, $(CH_2)_nSC_{1-4}$alkyl or $C(O)NR^4R^5$ or, when $R^0$ is $C_{1-3}$alkyl, $C_{1-3}$alkoxy, $C_{1-3}$alkoxy substituted by one or more fluorine atoms, or $O(CH_2)_nNR^4R^5$, may also be H; $R^2$ is H; $R^3$ is methyl or $NH_2$; $R^4$ and $R^5$ are independently $C_{1-3}$alkyl or, together with the nitrogen atom to which they are attached, form a 5–6 membered saturated ring; and n is 1–3.

In another aspect the invention provides a process for preparing another group of compounds (group A1) wherein $R^0$ is F, methyl, $C_{1-2}$alkoxy, $OCHF_2$, or $O(CH_2)_nNR^4R^5$; $R^1$ is methylsulphonyl, $OCHF_2$, $O(CH_2)_nCO_2C_{1-4}$alkyl, $O(CH_2)_nSCH_3$, $(CH_2)_nNR^4R^5$, $(CH_2)_nSCH_3$ or $C(O)NR^4R^5$ or, when $R^0$ is methyl, $C_{1-2}$alkoxy, $OCHF_2$, or $O(CH_2)_nN(CH_3)_2$, may also be H; $R^2$ is H; $R^3$ is methyl or $NH_2$; $R^4$ and $R^5$ are both methyl or, together with the nitrogen atom to which they are attached, form a 5–6 membered saturated ring; and n is 1–2.

In another aspect the invention provides a process for preparing a compound of formula (I) within group (group A2) wherein $R^0$ is F, $C_{1-3}$alkoxy or $C_{1-3}$alkoxy substituted by one or more fluorine atoms; $R^1$ is $C_{1-4}$alkylsulphonyl, $C_{1-4}$alkoxy substituted by one or more fluorine atoms or, when $R^0$ $C_{1-3}$alkoxy or $C_{1-3}$alkoxy substituted by one or more fluorine atoms, may also be H; $R^2$ is H; and $R^3$ is methyl or $NH_2$.

In another aspect the invention provides a process for preparing a compound of formula (I) within groups A, A1 and A2, wherein $R^0$ is preferably at the 3- or 4-position of the phenyl ring and $R^2$ is at the 6-position of the pyridazine ring.

In another aspect the invention provides a process for preparing the compound 2-(4-ethoxy-phenyl)-3-(4-methanesulfonyl-phenyl)-pyrazolo[1,5-b]pyridazine and pharmaceutically acceptable derivatives thereof.

Compounds of formula (II), including derivatives corresponding to pharmaceutically acceptable derivatives of formula (I), may be prepared by any method known in the art for the preparation of compounds of analogous structure.

The present invention provides a particularly advantageous process for the preparation of compounds of formula (II), as illustrated in Scheme 1 that follows. The reaction conditions and reagents mentioned in Scheme 1 are by way of example only. In scheme 1, $R^0$ to $R^3$ are as defined for formula (I) above; Ph is phenyl; and $X^-$ is a counterion.

Scheme 1

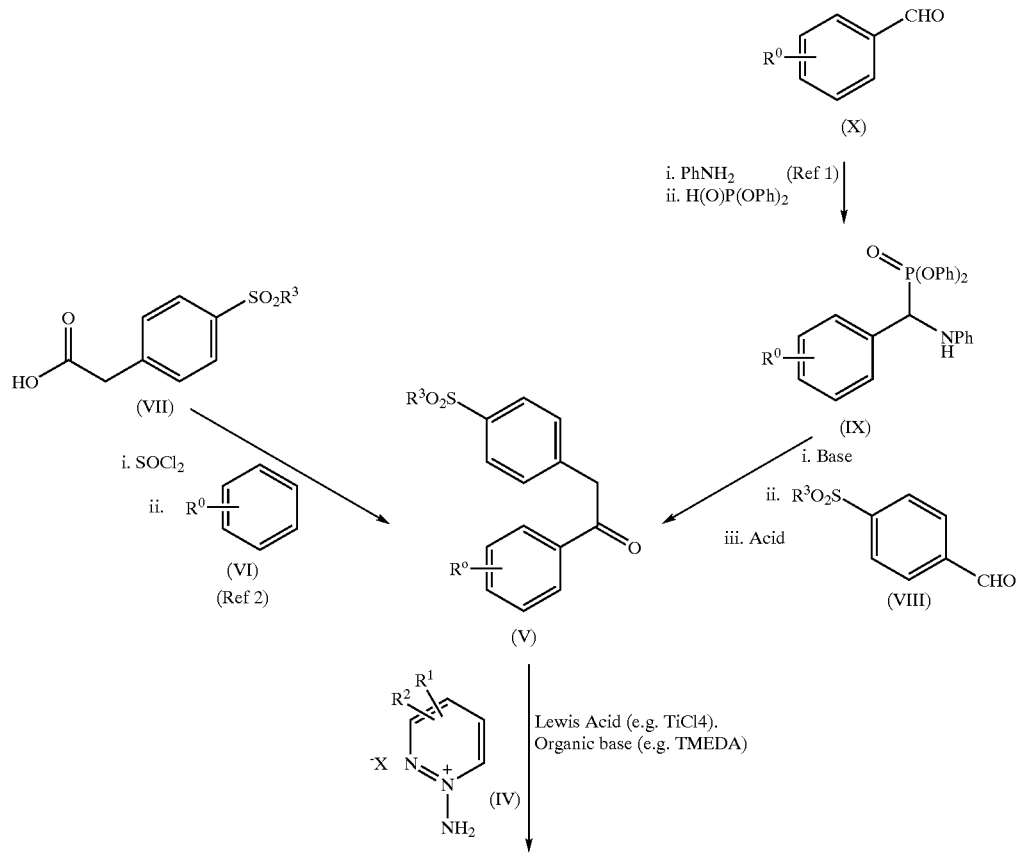

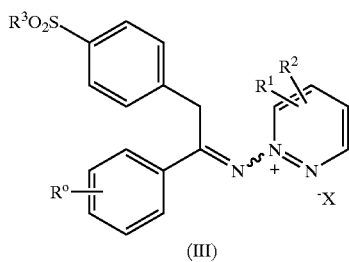

(III)

↓ Base (Ref 3)

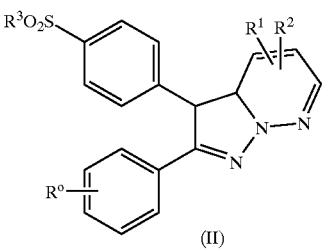

(II)

Ref 1 H. Zimmer, J. P. Bercz, Liebigs Ann. Chem. 1965, 686, 107–114, incorporated herein by reference.

Ref 2 Friedel Crafts acylation in the presence of a Lewis acid (e.g. AlCl$_3$).

Ref 3 Suitable inorganic bases include alkali hydroxides (e.g. NaOH); suitable organic bases include amines (e.g. N,N,N,N-tetramethylethylenediamine).

It will be appreciated by those skilled in the art that the imines of formula (III) prepared from the ethanones of formula (V) need not necessarily be isolated and may be employed in situ in the preparation of compounds of formula (II).

The compounds of formula (II) themselves need not necessarily be isolated and may be employed in situ in the preparation of compounds of formula (I), as described hereinabove.

Counterion X$^-$ in the N-aminopyridazinium salts of formula (IV) is conveniently a halide (e.g. I$^-$) or, more preferably, hexafluorophosphate (PF$_6{}^-$). N-Aminopyridazinium hexafluorophosphate salts of formula (IV) are novel and their use according to Scheme 1 is surprisingly advantageous. Thus N-aminopyridazinium hexafluorophosphate salts of formula (IV) are easily prepared and enable the conversion of ethanones of formula (V) to compounds of formula (II) via imines of formula (III) to proceed easily and in high yield.

Accordingly, in a further aspect the invention provides N-aminopyridazinium hexafluorophosphate salts of formula (IV) wherein R$^0$ to R$^3$ are as defined for formula (I) above, in particular N-aminopyridazinium hexafluorophosphate.

It will be appreciated by those skilled in the art that compounds of formula (II) may exist as a number of isomers, for example, as follows:

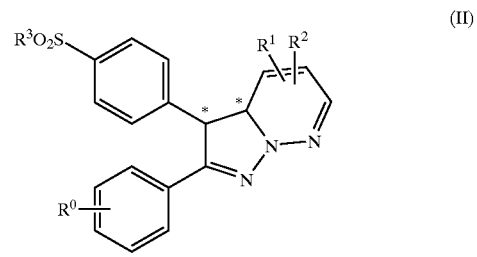

(II)

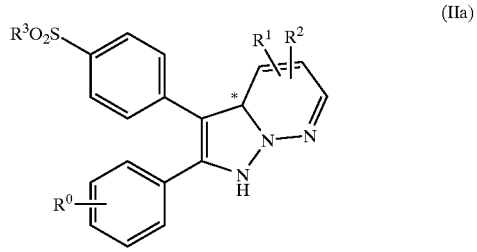

(IIa)

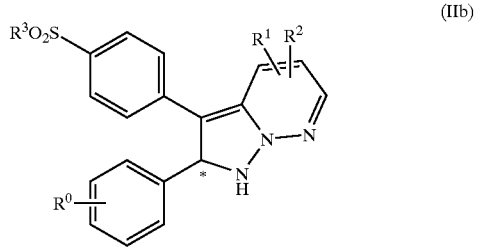

(IIb)

It will be further appreciated by those skilled in the art that such isomers may under certain conditions exist as an equilibrating mixture.

It will be still further appreciated by those skilled in the art that the compounds of formula (II) contain at least one chiral centre, designated by * therein, and that such compounds exist in the form of a pair of optical isomers (i.e. enantiomers).

It is to be understood that the present invention encompasses all isomers of the compounds of formula (II) and pharmaceutically acceptable derivatives thereof, including all positional, geometric, tautomeric, optical and diastereomeric forms, and mixtures thereof (e.g. racemic mixtures).

N-Aminopyridazinium halides of formula (IV) are either known compounds or may be prepared by literature methods such as those described in, for example, Y Kobayashi et al, Chem Pharm Bull, (1971), 19(10), 2106–15; T. Tsuchiya, J. Kurita and K. Takayama, Chem. Pharm. Bull. 28(9) 2676–2681 (1980); and K Novitskii et al, Khim Geterotskil Soedin, 1970 2, 57–62; all incorporated herein by reference.

N-Aminopyridazinium hexafluorophosphates of formula (IV) may be prepared by reacting the corresponding N-aminopyridazinium sulphate with hexafluorophosphoric acid or a suitable salt thereof (e.g. potassium hexafluorophosphate or ammonium hexafluorophosphate). The aforementioned sulphates may be prepared from pyridazine by conventional means.

Compounds of formula (VII) are either known compounds or may be prepared by literature methods such as those described in, for example, H Forrest, A Fuller, J Walker, J Chem Soc., 1948, 1501; R Dohmori, Chem Pharm Bull., 1964, (12), 591; and R Bromilow, K Chamberlain, S Patil, Pestic. Sci., 1990, (30), 1.

Compounds of formulae (VII), (VIII) and (X) are either known compounds or may by prepared from known compounds by conventional chemistry.

As will be appreciated by those skilled in the art it may be necessary or desirable at any stage in the synthesis of compounds of formula (I) to protect one or more sensitive groups in the molecule so as to prevent undesirable side reactions.

The protecting groups used in the preparation of compounds of formula (I) may be used in conventional manner. See, for example, those described in 'Protective Groups in Organic Synthesis' by Theodora W. Green and Peter G M Wuts, second edition, (John Wiley and Sons, 1991), incorporated herein by reference, which also describes methods for the removal of such groups.

Certain intermediates described above are novel compounds, and it is to be understood that all novel intermediates herein form further aspects of the present invention. Compounds of formula (II), (III) and (V), especially those compounds wherein $R^0$ is ethoxy, $R^1$ and $R^2$ are H, and $R^3$ is methyl, are key intermediates and represent a particular aspect of the present invention.

Conveniently, compounds of formula (I) are isolated following work-up in the form of the free base. Pharmaceutically acceptable acid addition salts of the compounds of formula (I) may be prepared using conventional means.

Solvates (e.g. hydrates) of a compound of formula (I) may be formed during the work-up procedure of one of the aforementioned process steps.

When a particular isomeric form of a compound is desired the required isomer may conveniently be separated using preparative high performance liquid chromatography (h.p.l.c.).

The following Examples illustrate, but do not in any way limit, the invention. All temperatures are in °C. Flash column chromatography was carried out using Merck 9385 silica. Thin layer chromatography (Tlc) was carried out on silica plates. NMR was carried out on a Bruker 400 MHz spectrometer, unless otherwise stated. Chemical shifts are given, with respect to tetramethylsilane as internal chemical shift reference, in δ ppm. The following abbreviations are used: Me, methyl; Et, ethyl; Ph, phenyl; IMS, industrial methylated spirits; TMEDA, N,N,N,N-tetramethylethylenediamine; DCM, dichloromethane; TFA, trifluoroacetic acid; s, singlet; d, doublet; t, triplet and m, multiplet.

EXAMPLE 1

N-Aminopyridazinium hexafluorophosphate

A solution of hydroxylamine-O-sulfonic acid (73.4 g) in water (80 mL) and a separate solution of potassium carbonate (65.5 g) in water (80 mL) were added concurrently dropwise to a solution of pyridazine (40.0 g) in water (120 mL) at 50° C., maintaining a reaction mixture pH of 3.5–4.0. The reaction mixture was then heated at 40° C. for 2 hours to give a solution of N-aminopyridazinium sulfate, which was subsequently cooled to 20° C. and filtered. The filtrate was added dropwise to a solution of potassium hexafluorophosphate (91.9 g) in water (460 mL) at 50° C. The resulting suspension was slowly cooled to 5° C. over a 2 hour period, stirred for 30 minutes and the product isolated by filtration. The filtercake was washed portionwise with water (320 mL) and the product dried in vacuo at 40° C. to give the title compound as a white crystalline solid (69.9 g, 58%).

$^1$H-NMR (CDCl$_3$); δ8.11(1H) m, J=8.4 Hz, J=5.4 Hz; δ8.46(1H) m, J=8.4 Hz, J=6.4 Hz; δ9.09(1H) d, J=6.4 Hz; δ9.24(1H) m, J=5.4 Hz;δ9.84(2H, NH$_2$) s. $^{19}$F-NMR (CDCl$_3$); δ70.55 (6F, PF$_6^-$) d, J$_{P-F}$=711 Hz.

EXAMPLE 2

N-Aminopyridazinium hexafluorophosphate

By using ammonium hexafluorophosphate (50.9 g) in water (50 mL), the title compound was obtained as a white crystalline solid (51.7 g, 68.7% based on pyridazine) in the manner of Example 1 and was spectroscopically identical thereto.

EXAMPLE 3

N-Aminopyridazinium hexafluorophosphate

By using a 60%w/w aqueous solution of hexafluorophosphoric acid (15.2 g), the title compound was obtained as a white crystalline solid (10.4 g, 68.8% based on pyridazine) in the manner of Example 1 and was spectroscopically identical thereto.

EXAMPLE 4

1-(4-Ethoxyphenyl)-2-[4-(methylsulfonyl)phenyl]ethanone

To a stirred suspension of 4-methylsulfonylphenylacetic acid[1] (10 g) in DCM (80 mL) was added dimethylformamide (0.18 mL). The mixture was heated to 30° C., treated with thionyl chloride (3.6 mL) and stirred for 1½ hours. The resulting solution was cooled to 15° C., treated with granular aluminium chloride (11.8 g) and stirred for further 15 minutes. Ethoxybenzene (7.1 mL) was added and the resultant mixture was warmed to 20° C. and stirred for 2 hours. The reaction mixture was cooled to 10° C. and treated dropwise with IMS (17 mL). The mixture was then diluted with DCM (120 mL) and water (60 mL) was then added over 20 minutes. The mixture was warmed to 30° C. and the layers separated. The organic layer was washed with 5M hydrochloric acid (2×40 mL), saturated sodium bicarbonate solution (40 mL) and then concentrated by distillation at atmospheric pressure to 40 mL. The mixture was cooled to 22° C. and aged for 18 hours. The product was isolated by filtration, washed with DCM:iso-octane (1:1, 2×20 mL) and dried in vacuo at 40° C. to give the title compound as a white crystalline solid (10.3 g, 69%). MH+ 319

$^1$H-NMR (CDCl$_3$) δ:7.98(m, J=9.1 Hz, 2H, 2× p-di-substituted aromatic CH); 7.91 (m, J=8.5 Hz, 2H, 2× p-di-substituted aromatic CH); 7.47(m, J=8.5 Hz, 2H, 2× p-di-substituted aromatic CH); 6.95(m, J=9.1 Hz, 2H, 2× p-di-substituted aromatic CH); 4.34(s, 2H, CH$_2$); 4.12(q, J=7.2 Hz, 2H, ethoxy-CH$_2$); 3.05(s, 3H, CH$_3$); 1.45(t, J=7.2 Hz, 3H, ethoxy-CH$_3$).

Ref 1: H Forrest, A Fuller, J Walker, J Chem Soc., 1948, 1501

EXAMPLE 5

A solution of 1-(4-ethoxyphenyl)-2-[4-(methylsulfonyl) phenyl]ethanone (0.5 g) in DCM (10 mL) was treated with triethylamine (0.22 mL) followed by titanium tetrachloride (0.52 mL). To the resultant deep red solution was added N-aminopyridazinium iodide[1] (0.26 g) and the mixture was heated under reflux for 18 hours. The reaction mixture was cooled to about 20° C. and treated dropwise with water (5 mL). The organic phase was washed with sodium hydroxide solution (2N, 5 mL), concentrated to dryness and a sample of the resulting crude solid analysed by HPLC-NMR.

Ref: 1 Y Kobayashi et al, Chem Pharm Bull, (1971) 19(10), 2106–15

| Column | Inertsil ODS-2 20 cm × 0.46 cm (5 μM) |  |
|---|---|---|
| Flow rate | 1 mL/minute |  |
| Detection | UV and NMR (Bruker DRX600 NMR Spectrometer) |  |
| Time (min) | MeCN + 0.05% v/v TFA (%) | D$_2$O + 0.05% v/v TFA (%) |
| 0 | 10 | 90 |
| 10 | 10 | 90 |
| 20 | 90 | 10 |
| 25 | 90 | 10 |
| 26 | 10 | 90 |

Two peaks were observed and characterised as follows:

a) Rt 9.74 min: The imine of formula (III) wherein R$^0$ is OEt, R$^1$ and R$^2$ are H and R$^3$ is Me:

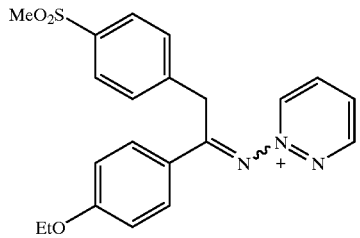

$^1$H-NMR (MeCN/D$_2$O) δ9.45(1H) d, J = 6Hz; δ9.36(1H) d, J = 6Hz; δ8.60(1H) m, J = 8Hz, J = 6Hz; δ8.44(1H) m, J = 8Hz, J = 6Hz; δ8.03(2H) d, J = 8Hz; δ7.79(2H) d, J = 8.2Hz; δ7.42(2H) d, J = 8.2Hz; δ7.05(2H) d, J = 8.2Hz; δ4.28(2H) s; δ4.13(2H) q, J = 7.0Hz; δ3.12(3H) s; δ1.35(3H) t, J = 7.0Hz; M 396 b) Rt 15.17 min: 2-(4-Ethoxyphenyl)-3-(4-methanesulfonyl-phenyl)-3,3a-dihydro-pyrazolo[1,5-b]pyridazine (co-elutes with 1-(4-ethoxyphenyl)-2-[4-(methylsulfonyl)phenyl]ethanone)

$^1$H-NMR (CH$_3$CN/D$_2$O) δ8.02 (2H) d, J=8.8 Hz; δ7.87 (2H) d, J=7.6 Hz; δ7.51(2H) d, J=7.6 Hz; δ7.02 (2H) d, J=8.8 Hz; δ6.72 (1H) m; δ5.85 (1H) m; δ5.56 (1H) m; δ4.87 (1H) d, J=10.6 Hz; δ4.69 (1H) m; δ4.12 (2H) q, ethyl (partially obscured under water peak); δ3.12 (3H) s; δ1.37 (3H) t, J=7.0 Hz; MH+ 396.

The skilled artisan will appreciate that the title compound may under certain conditions exist as an equilibrating mixture (discussed above on pages 7 & 8).

EXAMPLE 6

2-(4-Ethoxy-phenyl)-3-(4-methanesulfonyl-phenyl)-pyrazolo[1,5-b]pyridazine (i) 2-(4-Ethoxyphenyl)-3-(4-methanesulfonyl-phenyl)-3,3a-dihydro-pyrazolo[1,5-b]pyridazine A solution of 1-(4-ethoxyphenyl)-2-(4-methanesulfonyl-phenyl)-ethanone (0.25 g) in DCM (5 mL) was treated with triethylamine (0.11 mL) followed by titanium tetrachloride (0.26 mL). To the resultant deep red solution was added N-aminopyridazinium iodide (0.26 g) and the mixture was heated under reflux for 18 hours. The reaction mixture was cooled to 20° C. and treated dropwise with water (5 mL). The organic phase was separated, washed with sodium hydroxide solution (2N, 5 mL) and concentrated in vacuo to dryness. A sample of the residue was analysed by mass spectrometry, displaying a single major component, MH+ 396, corresponding to the title compound. The skilled artisan will appreciate that the title compound may under certain conditions exist as an equilibrating mixture (discussed above on pages 7 and 8).

(ii) 2-(4-Ethoxy-phenyl)-3-(4-methanesulfonyl-phenyl)-pyrazolo[1,5-b]pyridazine

The residue from Example 6(i), 2-(4-ethoxyphenyl)-3-(4-methanesulfonyl-phenyl)-3,3a-dihydro-pyrazolo[1,5-b]pyridazine, was redissolved in DCM (5 mL) and palladium on carbon (10% wt, 0.25 g) was added. The mixture was heated under reflux for 18 hours, whereupon analysis of the mixture by mass spectrometry showed the presence of a main component, MH+ 394, corresponding to the title compound. The reaction mixture was purified directly by silica gel chromatography (ethyl acetate/cyclohexane 2:1) to give the title compound as a white solid (0.181 g, 59%). MH+ 394

$^1$H-NMR (CDCl$_3$)δ: 8.30(d of d, J=4.4 Hz, J=1.9 Hz, 1H, aromatic CH); 7.98(m, J=8.5 Hz, 2H, 2× p-di-substituted aromatic CH); 7.91(d of d, J=9.1 Hz, J=1.9 Hz, 1H, aromatic CH); 7.58(m, J=8.5 Hz, 2H, 2× p-di-substituted aromatic CH); 7.55(m, J=8.8 Hz, 2H, 2× p-di-substituted aromatic CH); 7.07(d of d, J=9.1 Hz, J=4.4 Hz, 1H); 6.89(m, J=8.8 Hz, 2H, 2× p-di-substituted aromatic CH); 4.06(q, J=7.0 Hz, 2H, ethoxy-CH$_2$); 3.13(s, 3H, CH$_3$); 1.43(t, J=7.0 Hz, 3H, ethoxy-CH$_3$).

EXAMPLE 7

2-(4-Ethoxyphenyl)-3-(4-methanesulfonyl-phenyl)-pyrazolo[1,5-b]pyridazine

Titanium tetrachloride (12.0 mL) was added to a stirred suspension of 1-(4-ethoxyphenyl)-2-(4-methanesulfonyl-phenyl)-ethanone (10.0 g), N-aminopyridazinium hexafluorophosphate (8.3 g) and triethylamine (4.4 mL) in DCM (200 mL) at 20° C. and the reaction mixture heated at 40° C. for 4.5 hours. The reaction mixture was cooled to 28° C., treated dropwise with TMEDA (2.4 mL) and heated at 40° C. for 18 h to give a solution of the imine of Example 5(a). The reaction was cooled to 25° C., treated dropwise with further TMEDA (21.3 mL) and stirred at 25° C. for 3 hours to give a solution of (2-(4-ethoxyphenyl)-3-(4-methanesulfonyl-phenyl-3,3a-dihydro-pyrazolo[1,5-b]pyridazine). Iodine (8.0 g) was added and the reaction mixture stirred at 25° C. for 20 hours. IMS (25 mL) was added dropwise and the reaction mixture was then concentrated to 16 volumes by distillation at atmospheric pressure. The reaction was cooled to 30° C. and then treated with 3.33M hydrochloric acid (150 mL). The organic phase was separated and the aqueous phase further extracted with DCM (60 mL). The combined organic extracts were treated with charcoal (5 g) and concentrated to 5 volumes by distillation at atmospheric pressure. The concentrate was diluted with ethyl acetate (200 mL) and reconcentrated to 5 volumes by distillation at atmospheric pressure. The concentrate was further diluted with ethyl acetate (150 mL), heated to 60° C., filtered through a pad of celite, and the celite filtercake washed with warm ethyl acetate (100 mL). The combined filtrate and washes were heated to 60° C., washed with 2M sodium hydroxide (50 mL), 20% aqueous sodium thiosulfate (2×50 mL), water (2×50 mL) and concentrated to 4 volumes by distillation at atmospheric pressure. The slurry was stirred overnight at ambient temperature and then at 5° C. for 3.5 hours. The product was isolated by filtration, the filtercake washed with cold ethyl acetate (20 mL) and the product dried in vacuo at 45° C. to give the title compound as a pale brown crystalline solid (8.8 g, 71%). MH$^+$ 394

$^1$H-NMR (CDCl$_3$)δ: 8.30(d of d, J=4.4 Hz, J=1.9 Hz, 1H, aromatic CH); 7.98(m, J=8.5 Hz, 2H, 2× p-di-substituted aromatic CH); 7.91(d of d, J=9.1 Hz, J=1.9 Hz, 1H, aromatic CH); 7.58(m, J=8.5 Hz, 2H, 2× p-di-substituted aromatic CH); 7.55(m, J=8.8 Hz, 2H, 2× p-di-substituted aromatic CH); 7.07(d of d, J=9.1 Hz, J=4.4 Hz, 1H); 6.89(m, J=8.8 Hz, 2H, 2× p-di-substituted aromatic CH); 4.06(q, J=7.0 Hz, 2H, ethoxy-CH$_2$); 3.13(s, 3H, CH$_3$); 1.43(t, J=7.0 Hz, 3H, ethoxy-CH$_3$).

EXAMPLE 8

2-(4-Ethoxyphenyl)-3-(4-methanesulfonyl-phenyl)-pyrazolo[1,5-b]pyridazine

Titanium tetrachloride (26 mL) was added to a stirred suspension of 1-(4-ethoxyphenyl)-2-(4-methanesulfonyl-phenyl)-ethanone (75.0 g), N-amino-pyridazinium hexafluorophosphate (59.6 g) in DCM (1125 mL) at about 20° C. N-Methyl-pyrrolidinone (23 mL) was added and TMEDA (50 mL) was added over a period of about 4 hours and the reaction mixture heated at 40° C. for 4.5 hours. The reaction mixture was stirred at about 20° C. for about 2 hours and further TMEDA (93 mL) was added over about 15 minutes. The mixture was stirred for about 18 hours and iodine (63 g) was added. After about a further 5 hours, IMS (55 mL) was added, followed by 3.3M hydrochloric acid (1125 mL) and the layers were separated. The organic extract was further washed with 3.3M hydrochloric acid (375 mL), aqueous sodium carbonate solution (20% w/v, 375 mL), aqueous sodium thiosulfate solution (20% w/v, 2×375 mL) and aqueous sodium chloride solution (3% w/v, 2×375 mL). The organic extract was then concentrated by distillation to a residual volume of about 450 mL and iso-octane (about 187 mL) was added at about 38° C. The resultant slurry was cooled to about 0–5° C. and filtered. The crude product was washed with DCM/iso-octane (1:1, 2×150 mL) and iso-octane (400 mL), dried, and then dissolved in acetone (1200 mL). This solution was heated to about 50° C. and treated with charcoal (19 g) for about 1 hour before filtering. The charcoal was washed with hot acetone (750 mL) and the combined filtrates and washings were concentrated by distillation to a residual volume of about 825 mL. Further acetone (375 ml) was added to the concentrate, which was concentrated again to a residual volume of about 825 mL. Maintaining the temperature at about 50° C., water (450 mL) was added over about 1 hour, causing the product to crystallise. After cooling the slurry to about 0–5° C. the product was isolated by filtration, washed with chilled acetone/water (1:1, 2×150 mL), and dried in vacuo at 65° C. to give the title compound as a pale yellow crystalline solid (63.6 g, 68.6%), spectroscopically identical to the product of Example 7.

EXAMPLE 9

2-(4-Ethoxyphenyl)-3-(4-methanesulfonyl-phenyl)-3,3a-dihydro-pyrazolo[1,5-b]pyridazine Titanium tetrachloride (3.45 mL) was added to a stirred mixture of 1-(4-ethoxyphenyl)-2-(4-methanesulfonyl-phenyl)-ethanone (10.0 g), N-amino-pyridazinium hexafluorophosphate (7.95 g) in dichloromethane (150 mL) at about 20° C. N-Methyl-pyrrolidinone (3.0 mL) was added at about 20° C. TMEDA (6.7 mL) was then added over a period of about 4 hours at about 20° C. After stirring the mixture for about 1 hour, a second portion of TMEDA (12.3 mL) was added over about 20 minutes, and the reaction mixture was stirred at about 20° C. for about 16 hours.

A sample of the reaction mixture was purified by mass-directed preparative HPLC:

Column: ODS-2 IK-5; 15×2 cm (5 μm)

Detection: Mass Spectroscopy (Micromass ZMD spectrometer)

Flow rate: 8 mL/min

Temp: Ambient

| Time (min) | water + 0.04% v/v TFA (%) | MeCN + 0.04% v/v TFA(%) |
|---|---|---|
| 0 | 50 | 50 |
| 15 | 10 | 90 |
| 25 | 10 | 90 |

Fraction Collection Trigger: m/z=396 (electrospray ionisation)

Fraction Collection Trigger Threshold: 2000 counts

Fractions containing compound exhibiting m/z 396 were combined and evaporated to dryness to give the title compound.

$^1$H-NMR (CDCl$_3$) δ7.88 (2H) d, J=8.3 Hz; δ7.59 (2H) d, J=8.8 Hz; δ7.39(2H) d, J=8.3 Hz; δ6.81 (2H) d, J=8.8 Hz; δ6.74 (1H) m; δ5.83 (1H) m; δ5.37 (1H) m; δ4.74 (1H) m, δ4.59 (1H) d, J=10.8 Hz; δ4.00 (2H) q, J=6.8 Hz; δ3.04 (3H) s; δ1.39 (3H) t, J=6.8 Hz; MH$^+$ 396.

What is claimed is:

1. A process for the preparation of a compound of formula (I)

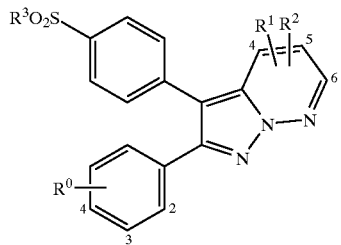

or a pharmaceutically acceptable salt or soluate thereof in which:

- $R^0$ is halogen, $C_{1-6}$alkyl, $C_{1-6}$alkoxy, $C_{1-6}$alkoxy substituted by one or more fluorine atoms, or $O(CH_2)_n NR^4R^5$;
- $R^1$ and $R^2$ are independently selected from H, $C_{1-6}$alkyl, $C_{1-6}$alkyl substituted by one or more fluorine atoms, $C_{1-6}$alkoxy, $C_{1-6}$hydroxyalkyl, $SC_{1-6}$alkyl, $C(O)H$, $C(O)C_{1-6}$alkyl, $C_{1-6}$alkylsulphonyl, $C_{1-6}$alkoxy substituted by one or more fluorine atoms, $O(CH_2)_nCO_2C_{1-6}$alkyl, $O(CH_2)_nSC_{1-6}$alkyl, $(CH_2)_nNR^4R^5$, $(CH_2)_nSC_{1-6}$alkyl or $C(O)NR^4R^5$; with the proviso that when $R^0$ is at the 4-position and is halogen, at least one of $R^1$ and $R^2$ is $C_{1-6}$alkylsulphonyl, $C_{1-6}$alkoxy substituted by one or more fluorine atoms, $O(CH_2)_nCO_2C_{1-6}$alkyl, $O(CH_2)_nSC_{1-6}$alkyl, $(CH_2)_nNR^4R^5$ or $(CH_2)_nSC_{1-6}$alkyl, $C(O)NR^4R^5$;
- $R^3$ is $C_{1-6}$alkyl or $NH_2$;
- $R^4$ and $R^5$ are independently selected from H, or $C_{1-6}$alkyl; and
- n is 1–4;

which comprises oxidising under conventional conditions the corresponding compound, of formula (II)

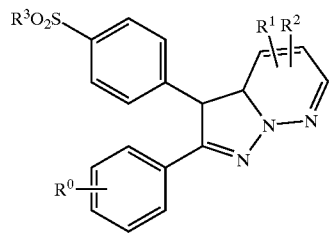

wherein $R^0$ to $R^3$ are as defined for formula (I) above.

2. A process according to claim 1 wherein the compound of formula (II) is prepared by treating an imine of formula (III)

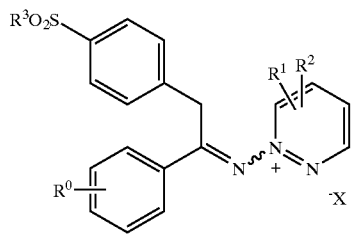

wherein ⁻X is a counterion;
with a base and wherein the imine of formula (III) is prepared by reacting an ethanone of formula (V)

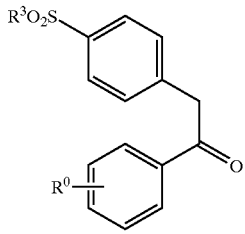

with an N-aminopyridazinium salt of formula (IV)

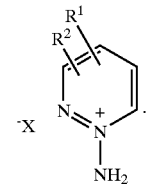

3. A process according to claim 1 for the preparation of 2-(4-ethoxy-phenyl)-3-(4-methanesulfonyl-phenyl)pyrazolo[1,5-b]pyridazine and pharmaceutically acceptable salt or soluate thereof which comprises oxidising under conventional conditions the compound of formula (II) that is MeSO₂—⟨phenyl⟩—pyrazolo-dihydropyridazine—⟨phenyl⟩—OEt 4. 2-(4-Ethoxyphenyl)-3-(4-methanesulfonyl-phenyl)-3,3a-dihydro-pyrazolo[1,5-b]pyridazine.

5. An imine of formula (III)

(III)

wherein $R^0$ is at the 4-position and is ethoxy; $R^1$ and $R^2$ are H; $R^3$ is methyl; and ⁻X is a counterion, which corresponds to a pharmaceutically acceptable salt or soluate of the compound of formula (I) of which the imine is a precursor.

6. 1-(4-ethoxyphenyl)-2-[4-(methylsulfonyl)phenyl] ethanone.

7. An N-aminopyridazinium salt of formula (IV)

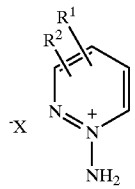

wherein:

$R^1$ and $R^2$ are independently selected from H, $C_{1-6}$alkyl, $C_{1-6}$alkyl substituted by one or more fluorine atoms, $C_{1-6}$alkoxy, $C_{1-6}$hydroxyalkyl, $SC_{1-6}$alkyl, $C(O)H$, $C(O)C_{1-6}$alkyl, $C_{1-6}$alkylsulphonyl, $C_{1-6}$alkoxy substituted by one or more fluorine atoms, $O(CH_2)_nCO_2C_{1-6}$ alkyl, $O(CH_2)_nSC_{1-6}$alkyl, $(CH_2)_nNR^4R^5$, $(CH_2)_nSC_{1-6}$ alkyl or $C(O)NR^4R^5$; and —X is $PF_6^-$.

8. N-Aminopyridazinium hexafluorophosphate.

* * * * *